United States Patent [19]

Sakuta et al.

[11] Patent Number: 5,254,542
[45] Date of Patent: Oct. 19, 1993

[54] ORGANIC SILICON COMPOUNDS AND COSMETIC COMPOSITIONS

[75] Inventors: Koji Sakuta; Satoshi Kuwata, both of Annaka, Japan

[73] Assignee: Shin-Etsu Chemical Co., Ltd., Tokyo

[21] Appl. No.: 765,305

[22] Filed: Sep. 25, 1991

[30] Foreign Application Priority Data

Sep. 25, 1990 [JP] Japan .................. 2-254971

[51] Int. Cl.$^5$ ............................................. A01N 25/02
[52] U.S. Cl. ....................................... 514/63; 514/844; 548/110; 556/436; 556/443
[58] Field of Search .................. 548/110; 514/63; 511/844; 556/437, 443, 457, 436

[56] References Cited

U.S. PATENT DOCUMENTS

| | | | |
|---|---|---|---|
| 4,316,033 | 2/1982 | Ching | 548/110 |
| 4,328,346 | 5/1982 | Chung et al. | 548/110 |
| 4,349,602 | 9/1982 | Ching | 548/110 |
| 4,373,061 | 2/1983 | Ching | 524/837 |
| 4,495,360 | 1/1985 | Anthony | 556/436 |
| 4,696,969 | 9/1987 | Thimineur et al. | 524/762 |
| 4,803,254 | 2/1989 | Dunks et al. | 548/260 |
| 4,960,898 | 10/1990 | Sakuta et al. | 548/110 |
| 5,089,250 | 2/1992 | Forestier et al. | 514/63 |
| 5,102,707 | 4/1992 | Canivec et al. | 548/110 |
| 5,164,462 | 11/1992 | Yang | 548/110 |

FOREIGN PATENT DOCUMENTS

| | | |
|---|---|---|
| 0088842 | 9/1983 | European Pat. Off. . |
| 0282294 | 9/1988 | European Pat. Off. ............ 548/110 |
| 0389337 | 9/1990 | European Pat. Off. . |
| 1457966 | 11/1966 | France ............................... 548/110 |
| 2642968 | of 1990 | France . |
| 52-50074 | 12/1977 | Japan . |
| 57-21391 | 2/1982 | Japan . |
| 57-21432 | 2/1982 | Japan . |
| 58-10591 | 1/1983 | Japan . |
| 61-111360 | 5/1986 | Japan . |
| 62-187740 | 8/1987 | Japan . |
| 63-230681 | 9/1988 | Japan . |
| 2-243695 | 9/1990 | Japan . |
| 3-217420 | 9/1991 | Japan . |
| 3-287588 | 12/1991 | Japan ............................... 546/437 |
| 2077280 | 12/1981 | United Kingdom . |
| 2078242 | 1/1982 | United Kingdom . |

OTHER PUBLICATIONS

Sakuta et al. Chem. Abstr. vol. 114 entry 63532t abstracting EP388,218 (1990).

Canivenc et al. Chem. Abstr. vol. 113 entry 25059r (1990).

Primary Examiner—Donald G. Daus
Attorney, Agent, or Firm—Birch, Stewart, Kolasch & Birch

[57] ABSTRACT

Novel organic silicon compounds having a UV absorbing benzotriazole or benzophenone skeleton are provided comprising $R^1{}_3SiO_{\frac{1}{2}}$ and $SiO_2$ units as essential units, 0 to 20 mol % of $R^2SiO_{3/2}$ and $R^3{}_2SiO$ units, and 0 to 20 mol % of $R^3{}_2SiO$ units. The siloxane units are present in a molar ratio: $(R^1{}_3SiO_{\frac{1}{2}}+R^2SiO_{3/2}+R^3{}_2SiO)/SiO_2$ of from 0.5 to 1.5. At least one group of formulae (1) through (7) constitutes 1 to 33 mol % of the total quantity of the organic groups represented by $R^1$, $R^2$ and $R^3$ while the remainder is a monovalent saturated or unsaturated organic group or groups having 1 to 18 carbon atoms. Cosmetic compositions containing the same compounds have improved UV absorbing capacity.

20 Claims, 4 Drawing Sheets

ORGANIC SILICON COMPOUNDS AND COSMETIC COMPOSITIONS

This invention relates to novel organic silicon compounds having a benzotriazole or benzophenone skeleton, exhibiting improved ultraviolet absorption and film forming ability, and offering a preasant feel when blended in cosmetics. It also relates to cosmetic compositions containing the same.

BACKGROUND OF THE INVENTION

Heretofore, ultraviolet (UV) absorbents having a benzotriazole or benzophenone skeleton have been used as additives to medical and cosmetic compositions as well as resin compositions.

However, these compounds that have a benzotriazole or benzophenone skeleton and are useful as UV absorbents suffered from various problems. Specifically the amount of the absorbents blended into a composition was limited due to their poor dispersion and solubility in base compounds. Moreover, bleeding could occur due to their dispersion instability.

Various proposals were made for improving the dispersion and dissolution of these compounds. For example, Japanese Patent Application Laid-open (JP-A) Nos. 21391/1982, 21432/1982, 10591/1983, 213075/1983, 111360/1986, and 187740/1987 disclose compounds of benzotriazole or benzophenone skeleton having alkoxysilyl groups incorporated therein. Due to the presence of alkoxysilyl groups, these compounds are susceptible to hydrolysis and lack stability. Medical and cosmetic compositions having these compounds blended therein have an unpleasant feel since the hydrolyzed products of these compounds are stimulative to the skin and mucous membranes.

For further improvement in stability, hydrolysis resistant compounds were proposed as disclosed in Japanese Patent Publication No. 50074/1977, JP-A 230681/1988, and Japanese Patent Application Nos. 64485/1989 and 12874/1990, for example. These compounds are unsusceptible to hydrolysis, but oily and less likely to form films.

JP-A 21391/1982 discloses a method for forming films by applying compounds having a benzotriazole or benzophenone skeleton to plastics and subjecting the compounds to hydrolysis to form films. This method is less consistent since film forming rate and film state vary with the surrounding atmosphere. Also, a hygienic problem occurs since alcohols are generated upon film formation.

There is a need for developing UV absorbing compounds free of the above-mentioned problems.

SUMMARY OF THE INVENTION

Therefore, an object of the present invention is to provide novel and improved organic silicon compounds capable of absorbing UV, forming a film, and providing a pleasant feel when blended in cosmetic and similar compositions. Another object of the present invention is to provide a cosmetic composition containing the same.

We have found that by starting with a compound having a UV absorbing benzotriazole or benzophenone skeleton represented by the following formula (8) or (9):

(8)

(9)

converting the phenol component of the compound into an allyl ether derivative and if desired, further converting the allyl ether derivative into an allyl derivative through thermal rearrangement reaction, reacting either of the derivatives with a hydrosilane compound having a hydrolyzable halogen atom or alkoxy group, and then subjecting the reaction product to either a hydrolysis reaction with a hydrolyzable chlorosilane, chloropolysiloxane, alkoxysilane, alkoxypolysiloxane or alkoxy polysilicate or a polycondensation reaction with a non-hydrolyzable organopolysiloxane, their is obtained an organic silicon compound having a benzotriazole or benzophenone skeleton as defined below.

The present invention provides an organic silicon compound having a benzotriazole or benzophenone skeleton, comprising $R^1_3SiO_{\frac{1}{2}}$ and $SiO_2$ units as essential units and $R^2SiO_{3/2}$ and $R^3_2SiO$ units as optional units. The amounts of $R^2SiO_{3/2}$ and $R^3_2SiO$ units each range from 0 to 20 mol % of the entire compound. These siloxane units are present in a molar ratio: $(R^1_3SiO_{\frac{1}{2}}+R^2SiO_{3/2}+R^3_2SiO)/SiO_2$ of from 0.5 to 1.5. Among the organic groups represented by $R^1$, $R^2$ and $R^3$, 1 to 33 mol % of the total quantity thereof is selected from the groups of the following structural formulae (1) through (7), the remainder being a monovalent saturated or unsaturated organic group having 1 to 18 carbon atoms.

(1)

(2)

(3)

In formulae (1) through (7),

R[4] is a hydrogen atom or a monovalent saturated hydrocarbon group having 1 to 5 carbon atoms, R[5] is a monovalent saturated or unsaturated organic group having 1 to 18 carbon atoms, a halogen atom, or an alkoxy, carboxy, hydroxy, or amino group, R[6] is a hydrogen atom or a monovalent saturated or unsaturated hydrocarbon group having 1 to 10 carbon atoms, letter a is an integer of from 0 to 3, b is an integer of from 0 to 4, and c is an integer of from 0 to 5.

These organic silicon compounds having a benzotriazole or benzophenone skeleton have improved UV absorbing capacity and are capable of readily forming tack-free, crack-free, even films. When blended in cosmetic compositions, the compounds are well dispersible, soluble, and spreadable and give pleasant feel on use. Therefore, cosmetic compositions containing the organic silicon compounds are also contemplated herein.

DETAILED DESCRIPTION OF THE INVENTION

According to the present invention, organic silicon compounds are defined as comprising $R^1_3SiO_{\frac{1}{2}}$ and $SiO_2$ units as essential units and $R^2SiO_{3/2}$ and $R^3_2SiO$ units as optional units. The amounts of $R^2SiO_{3/2}$ and $R^3_2SiO$ units each range from 0 to 20 mol % of the entire compound. These siloxane units are present in a molar ratio:

$$(R^1_3SiO_{\frac{1}{2}} + R^2SiO_{3/2} + R^3_2SiO)/SiO_2$$

of from 0.5/1 to 1.5/1, preferably from 0.6/1 to 1.3/1. If this ratio is less than 0.5/1, the resulting compounds would form less even films which are too hard and susceptible to cracking. If this ratio is more than 1.5/1, the resulting compounds would become tacky.

Among the siloxane units, the $R^2SiO_{3/2}$ and $R^3_2SiO$ units each are contained in amounts of from 0 to 20 mol % of the entire compound, preferably from 0 to 10 mol % of the entire compound. More than 20 mol % would result in poor solubility in organic solvent, difficulty to handle, and increased tackiness.

$R^1$, $R^2$ and $R^3$ in the siloxane units of $R^1_3SiO_{\frac{1}{2}}$, $R^2SiO_{3/2}$ and $R^3_2SiO$ are organic groups. The organic silicon compounds of the invention contain at least one group of structural formulae (1) through (7) in an amount of 1 to 33 mol %, preferably 1 to 20 mol % based on the total moles of the organic groups. If this content is less than 1 mol %, no effective UV absorbing capacity is imparted. If this content exceeds 33 mol %, the resulting compounds would be less dispersible and soluble in a base medium.

In formulae (1) through (7), $R^4$ is a hydrogen atom or a monovalent saturated hydrocarbon group having 1 to 5 carbon atoms, $R^5$ is selected from monovalent saturated or unsaturated organic groups having 1 to 18 carbon atoms, preferably 1 to 10 carbon atoms, halogen atoms, alkoxy, carboxy, hydroxy, and amino groups, $R^6$ is a hydrogen atom or a monovalent saturated or unsaturated hydrocarbon group having 1 to 10 carbon atoms, preferably 1 to 8 carbon atoms, letter a is an integer of from 0 to 3, b is an integer of from 0 to 4, and c is an integer of from 0 to 5.

Examples of the group represented by $R^4$ include hydrogen atom, methyl, ethyl, propyl, butyl and pentyl groups. Examples of the group represented by $R^5$ include the same groups as represented by $R^1$ to $R^3$, which will be described later, chlorine, bromine, and fluorine atoms, and methoxy, ethoxy, carboxy, hydroxy and amino groups. Examples of the group represented by $R^6$ include hydrogen atom; aliphatic hydrocarbon groups such as methyl, ethyl, propyl, butyl, pentyl, hexyl, heptyl, octyl, nonyl and decyl groups; saturated cycloaliphatic hydrocarbon groups such as cyclopentyl and cyclohexyl groups; and aromatic hydrocarbon groups such as phenyl and tolyl groups.

The remaining organic groups represented by $R^1$, $R^2$ and $R^3$ are the same or different monovalent saturated or unsaturated organic groups having 1 to 18 carbon atoms, for example, aliphatic hydrocarbon groups such as methyl, ethyl, propyl, butyl, pentyl, hexyl, heptyl, octyl, nonyl, decyl, dodecyl, tetradecyl, hexadecyl, and octadecyl groups; saturated cycloaliphatic hydrocarbon groups such as cyclopentyl and cyclohexyl groups; and aromatic hydrocarbon groups such as phenyl and tolyl groups. Preferably, at least 50 mol % of the total moles of $R^1$, $R^2$ and $R^3$ is a methyl group, and most preferably, the remaining organic groups are solely methyl.

The organic silicon compounds of the invention can be synthesized by the following process, for example.

The starting material is a compound having UV absorbing capacity of the following formula (8) or (9).

The phenol component of this compound is converted into an allyl ether derivative. If desired, the allyl ether derivative is further converted into an allyl derivative through thermal rearrangement reaction. Either of the derivatives is reacted with a hydrosilane compound having a hydrolyzable halogen atom or alkoxy group (addition reaction). The reaction product is then subject to hydrolysis reaction with a hydrolyzable chlorosilane, chloropolysiloxane, alkoxysilane, alkoxypolysiloxane or alkoxy polysilicate or polycondensation reaction with a non-hydrolyzable organopolysiloxane. There is obtained an organic silicon compound having a benzotriazole or benzophenone skeleton as defined above.

Examples of the compounds of formulae (8) and (9) used as the starting material are given below.

-continued 2-(2'-hydroxyphenyl)-5-caboxybenzotriazole 2-(2'-hydroxy-5'-tert-butylphenyl)-5-aminobenzotriazole 2-hydroxybenzophenone 2,4-dihydroxybenzophenone 2-hydroxy-4-methoxybenzophenone 2-hydroxy-4-octoxybenzophenone 2,2'-dihydroxy-4,4'-dimethoxybenzophenone 2,2'-dihydroxy-4-methoxybenzophenone 2,2',4,4'-tetrahydroxybenzophenone

-continued

More illustratively, the compounds for formulae (8) and (9) can be reacted with halogenated ally compounds of the general formula: $CR^4{}_2\!=\!C(R^4)\!-\!CR^4{}_2\!-\!X$ wherein $R^4$ is as defined above and X is a chlorine atom, bromine atom, or iodine atom in basic conditions whereupon their phenol components are converted into allyl ether derivatives of the following general formulae (10) to (12).

Preferably, the compounds of formulae (8) and (9) are reacted with halogenated ally compounds by mixing them in a molar ratio of from 1:1 to 1:5, more preferably from 1:1 to 1:2 and heating at a temperature of 50° to 100° C. for about 1 to about 20 hours.

The allyl ether derivatives of formulae (10) to (12) can be converted into allyl derivatives of the following general formulae (13) to (16) through thermal rearrangement reaction.

The rearrangement reaction conditions are not critical, but desirably include a temperature of 150° to 300° C. and a time of from 1 to 5 hours.

The allyl ether derivatives or the allyl derivatives are then subject to addition reaction with hydrosilane compounds having a hydrolyzable halogen atom or alkoxy group by mixing them preferably in a molar ratio of 1:1 to 1:5, more preferably 1:1 to 1:2.

The hydrosilane compounds used herein are of the general formula:

$$HSiR^1_n(OR^1)_{3-n}$$

wherein $R^1$ is as defined above and n is equal to 0, 1 or 2, for example, alkoxysilanes such as trimethoxysilane, triethoxysilane, tripropoxysilane, methyldimethoxysilane, methyldiethoxysilane, methyldipropoxysilane, ethyldimethoxysilane, ethyldiethoxysilane, ethyldipropoxysilane, dimethylmethoxysilane, dimethylethoxysilane, dimethylpropoxysilane, diethylmethoxysilane, diethylethoxysilane, diethylpropoxysilane, phenyldimethoxysilane, phenyldiethoxysilane, phenyldipropoxysilane, diphenylmethoxysilane, diphenylethoxysilane, and diphenylpropoxysilane; and of the general formula:

$$HSiR^1_nX_{3-n}$$

wherein $R^1$ is as defined above, X is halogen, and n is equal to 0, 1 or 2, for example, chlorosilanes such as trichlorosilane, methyldichlorosilane, ethyldichlorosilane, dimethylchlorosilane, diethylchlorosilane, phenyldichlorosilane, and diphenylchlorosilane.

For the addition reaction, catalysts such as platinum compounds and palladium compounds are preferably added in catalytic amounts. Exemplary catalysts are chloroplatinic acid, rhodium complexes, and paladium complexes.

Prior to the addition reaction with hydrosilanes, the phenol component in the allyl ether derivative or allyl derivative molecule may be protected with an organic silicon group by reacting with a conventional silylating agent such as hexamethyldisilazane and N,O-bis(trimethylsilyl)-acetamide.

Finally, the addition reaction product is subject to hydrolysis reaction with a hydrolyzable chlorosilane, chloropolysiloxane, alkoxysilane, alkoxypolysiloxane or alkoxy polysilicate or polycondensation reaction with a non-hydrolyzable organopolysiloxane in a conventional manner. For example, hydrolysis or polycondensation reaction is carried out by charging a reactor with the addition reaction product, a hydrolyzable chlorosilane, chloropolysiloxane, alkoxysilane, alkoxypolysiloxane or alkoxy polysilicate or a non-hydrolyzable organopolysiloxane, organic solvent and acid, adding water to the reactor, and allowing the reaction to take place at room temperature or elevated temperatures. Alternatively, hydrolysis or polycondensation reaction is carried out by charging a reactor with water, organic solvent and acid, adding a mixture of the addition reaction product and a hydrolyzable chlorosilane, chloropolysiloxane, alkoxysilane, alkoxypolysiloxane or alkoxy polysilicate or a non-hydrolyzable organopolysiloxane to the reactor, and allowing the reaction to take place at room temperature or elevated temperatures. An end organic silicon compound is obtained in this way. In addition to the last-mentioned step, the organic silicon compounds of the invention can be obtained by hydrosilylating the addition reaction product with a resinous compound having a Si-H bond.

EXAMPLE

Examples of the present invention are given below by way of illustration and not by way of limitation.

EXAMPLE 1

A reactor was charged with 98.4 grams of 2-(2'-hydroxy-5'-methylphenyl)benzotriazole and 250 grams of toluene. To the reactor 127 grams of a methanol solution containing 28% by weight of sodium methoxide was gradually added through a dropping funnel. After stirring for 30 minutes at room temperature, the contents were heated to 70° to 85° C. for removing 100 grams of the solvent. The contents were cooled down to 40° C. in flowing air whereupon 106.4 grams of allyl bromide was gradually added through a dropping funnel. The reaction mixture was heated under reflux for 2 hours. After the formed salt was removed by filtration, the product was washed with water, the solvent removed in vacuum, and the residue distilled in vacuum. At this point, the rearranged product was directly obtained without isolating the allyl ether derivative or intermediate. That is, upon distillation, the whole contents were kept under reflux for rearrangement without taking out any fraction until the effluent temperature exceeded 200° C. In this way, there was obtained 106.4 grams of a fraction at a distillation temperature of 211° to 222° C. in a vacuum of 7 mmHg.

The fraction was recrystallized from 1000 grams of a solvent mixture of toluene and methanol in a weight ratio of 1:9. There was obtained 87.9 grams of an allyl derivative having the following formula (I).

It was a white needle crystal product having a melting point of 100° to 102° C.

Next, a reactor was charged with 50 grams of allyl derivative (I), 100 grams of toluene, and 35 grams of N,O-bis(trimethylsilyl)-acetamide and heated under reflux for 4 hours. After the solvent was removed in vacuum, the residue was distilled, yielding 60.0 grams of a derivative having the following formula (II).

It was a clear, pale yellow liquid having a melting point of 210° to 217° C. at a vacuum of 2 mmHg.

Next, a reactor was charged with 25.0 grams of derivative (II) and 30.0 grams of toluene. After the contents were heated to 80° C., 0.05 grams of a 2-propanol solution of 2% by weight chloroplatinic acid was added and 11 grams of trimethoxysilane was gradually added through a dropping funnel. After the completion of addition, the mixture was heated under reflux for 4 hours, and the solvent was removed in vacuum. Distillation of the residue yielded 24.7 grams of a derivative having the following formula (III).

It was a clear, reddish yellow liquid having a melting point of 230° to 240° C. at a vacuum of 4 mmHg.

Thereafter, a reactor was charged with 15.0 grams of derivative (III), 34.6 grams of Methyl Silicate 51 ® (methoxysilane oligomer, manufactured by Kolcoat K. K.), 19.6 grams of hexamethyldisiloxane, and 0.9 grams of methane sulfonate. To the reactor 11.1 grams of water was gradually added through a dropping funnel. After the completion of addition, the mixture was stirred for 30 minutes and after heated to 64° to 68° C., stirred for a further 5 hours. The reaction solution was cooled down to room temperature, combined with 50 grams of toluene, and washed with water. Removal of the solvent in vacuum resulted in 32.0 grams of an organic silicon compound in pale yellow solid form.

Figure 1:
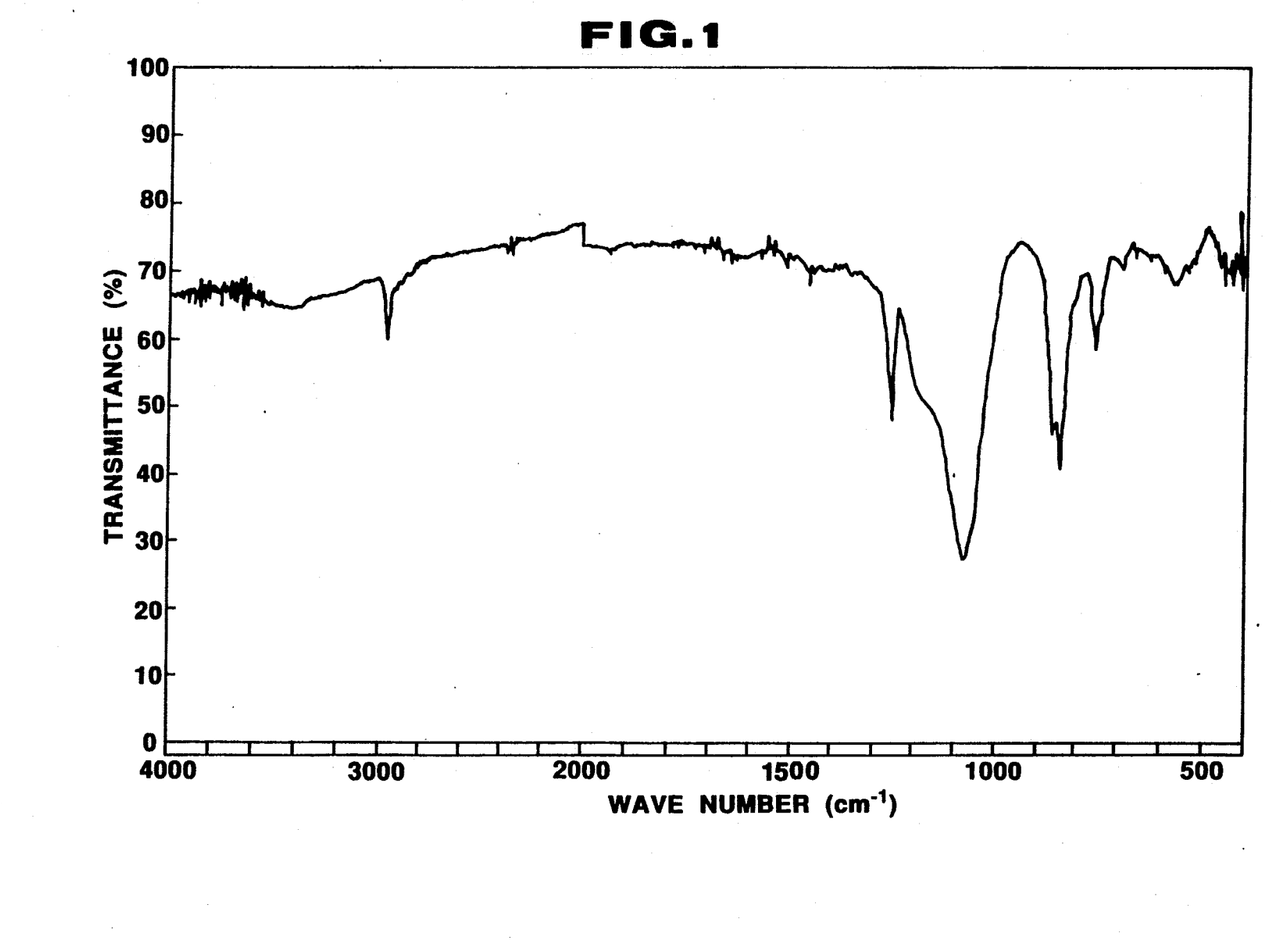
FIGS. 1 and 2 are the IR and UV absorption spectra of the organic silicon compound obtained in Example 1, respectively.
Figure 2:
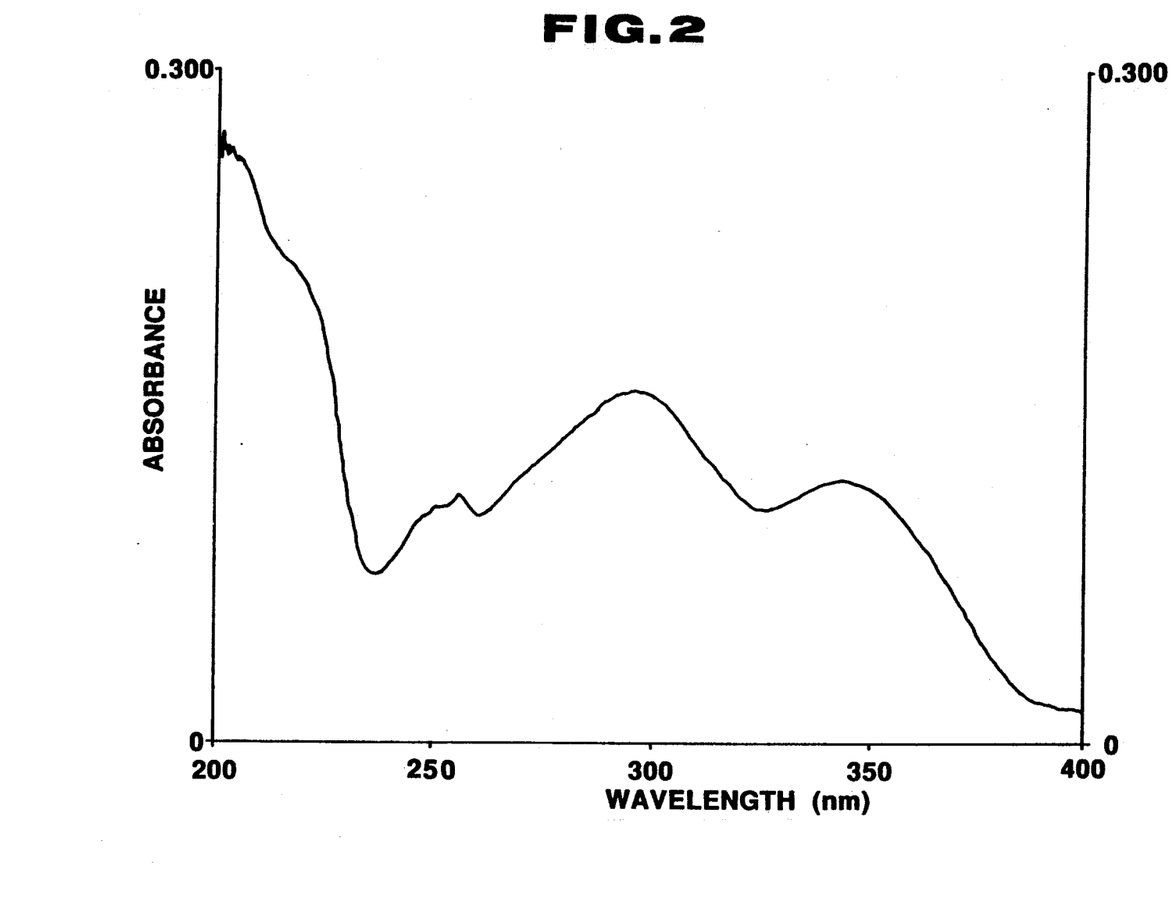

The IR and UV absorption spectra of the thus obtained organic silicon compound are shown in FIGS. 1 and 2. For the UV absorption spectroscopy, a solution containing 1.01 mg of the compound in 100 ml of ethanol was used.

This organic silicon compound was identified as consisting of three siloxane units: $(CH_3)_3SiO_{\frac{1}{2}}$, $RSiO_{3/2}$ and $SiO_2$ units wherein 4.1 mol % of the entire organic groups is a group represented by the following structural formula:

the siloxane units are present in a molar ratio: $[(CH_3)_3SiO_{\frac{1}{2}}+RSiO_{3/2}]/SiO_2=0.93$, and the content of $RSiO_{3/2}$ units is 5.7 mol % of the entire compound.

This compound was soluble in octamethylcyclotetrasiloxane. A solution containing 48% by weight of the compound therein was a yellow solution having a viscosity of 127 centistokes (cSt) at 25° C. Removal of the octamethylcyclotetrasiloxane from this solution left an even, tack-free, crack-free film.

EXAMPLE 2

A reactor was charged with 45.6 grams of 2-hydroxy-4-methoxybenzophenone and 300 grams of toluene. To the reactor 46.3 grams of a methanol solution containing 28% by weight of sodium methoxide was gradually added through a dropping funnel while stirring for 30 minutes at room temperature. While admitting nitrogen gas into the reactor, the reactor was heated by an oil bath at 100° C. for removing 48 grams of the solvent. The contents were cooled down to room temperature in flowing air whereupon 34.0 grams of allyl bromide and 100 grams of dimethylformamide were gradually added through a dropping funnel.

After the completion of addition, the reaction mixture was heated under reflux for 5 hours. The formed salt was removed by filtration and the product was washed with water. Further the solvent was removed in vacuum. The residue was heated at 240° to 250° C. in a vacuum of 35 mmHg for one hour and then distilled, yielding 46.2 grams of an allyl derivative of the following formula (IV).

The allyl derivative (IV) had a melting point of 221° to 225° C. in a vacuum of 9 mmHg.

Next, a reactor was charged with 39.2 grams of allyl derivative (IV), 40 grams of toluene, and 29.8 grams of N,O-bis(trimethylsilyl)acetamide and heated under reflux for 4 hours. After the solvent was removed in vacuum, the residue was distilled, yielding 48.7 grams of a derivative having the following formula (V).

It was a clear, pale yellow liquid having a melting point of 178° to 180° C. at a vacuum of 1 mmHg.

Next, a reactor as charged with 45.0 grams of derivative (V) and 50 grams of toluene. After the contents were heated to 80° C., 0.1 grams of a 2-propanol solution of 2% by weight chloroplatinic acid was added and 24.0 grams of trimethoxysilane was gradually added through a dropping funnel. After the completion of addition, the mixture was heated under reflux for 4 hours, and the solvent was removed in vacuum. Distillation of the residue yielded 55.6 grams of a derivative having the following formula (VI).

(VI)

It was a clear, slightly yellow liquid having a melting point of 198° to 203° C. at a vacuum of $3 \times 10^{-2}$ mmHg.

Thereafter, a reactor was charged with 34.4 grams of derivative (VI), 78.8 grams of Methyl Silicate 51® (methoxysilane oligomer, manufactured by Kolcoat K. K.), 44.6 grams of hexamethyldisiloxane, and 2.3 grams of methane sulfonate. To the rector 72.2 grams of water was gradually added through a dropping funnel. After the completion of addition, the mixture was stirred for 30 minutes and after heated to 64° to 68° C., stirred for a further 5 hours. The reaction solution was cooled down to room temperature, combined with 200 grams of toluene, and washed with water. Removal of the solvent in vacuum resulted in 58.3 grams of an organic silicon compound in pale yellow solid form.

Figure 3:
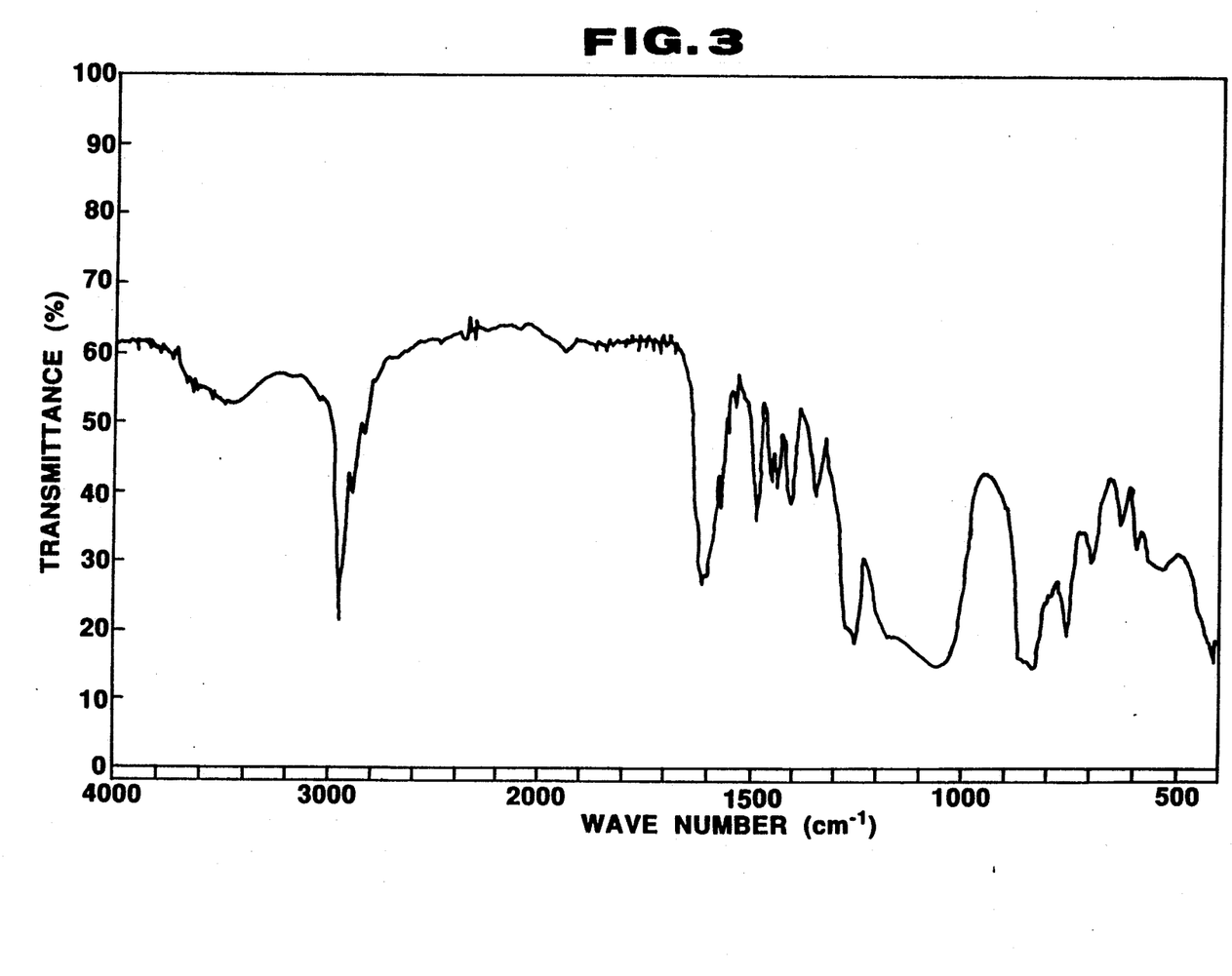
FIGS. 3 and 4 are the IR and UV absorption spectra of the organic silicon compound obtained in Example 2, respectively.
Figure 4:
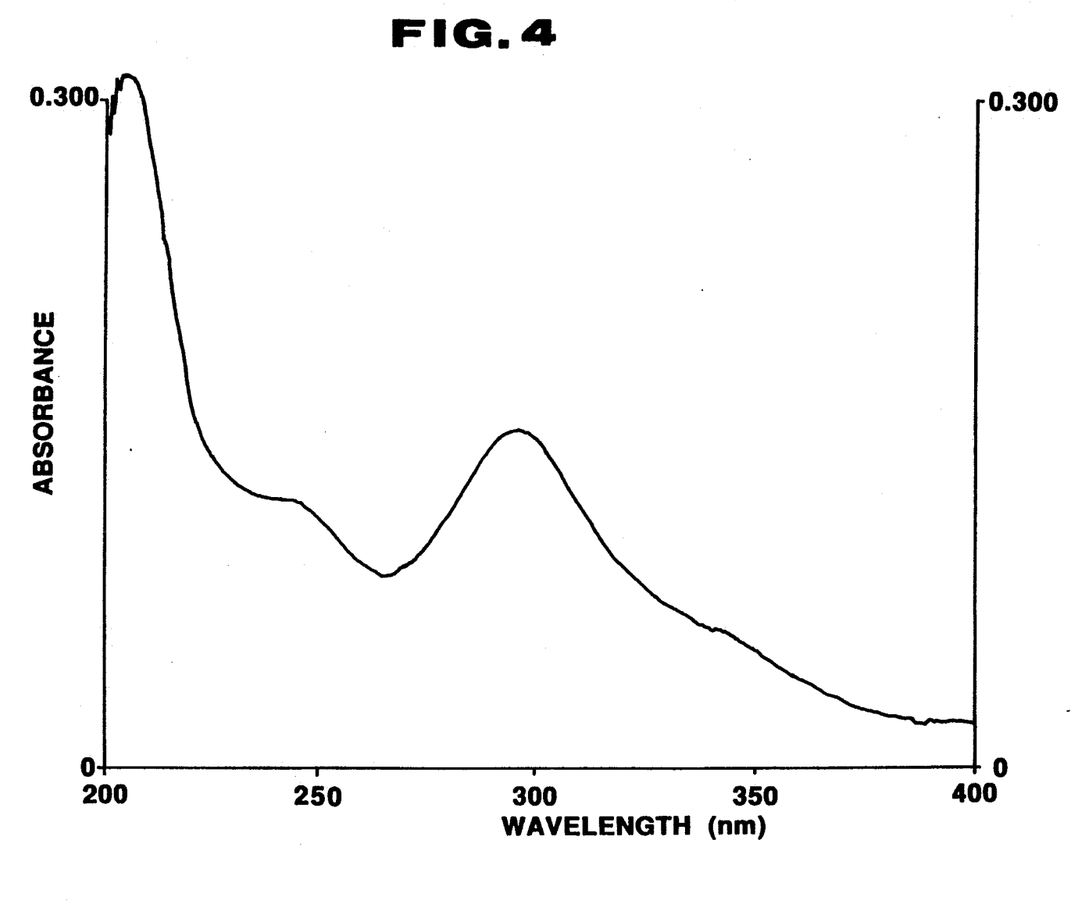

The IR and UV absorption spectra of the thus obtained organic silicon compound are shown in FIGS. 3 and 4, respectively. For the UV absorption spectroscopy, a solution containing 1.00 mg of the compound in 100 ml of ethanol was used.

This organic silicon compound was identified as consisting of three siloxane units: $(CH_3)_3SiO_{\frac{1}{2}}$ $RSiO_{3/2}$ and $SiO_2$ units wherein 4.1 mol % of the entire organic groups is a group represented by the following structural formula:

the siloxane units are present in a molar ratio: $[(CH_3)_3SiO_{\frac{1}{2}}+RSiO_{3/2}]/SiO_2=9.3$, and the content of $RSiO_{3/2}$ units is 5.7 mol % of the entire compound.

This compound was soluble in octamethylcyclotetrasiloxane. A solution containing 45% by weight of the compound therein was a yellow solution having a viscosity of 88 cSt at 25° C. Removal of the octamethylcyclotetrasiloxane from this solution left an even, tack-free, crack-free film.

The following examples illustrate the exemplary formulation of cosmetic products which were obtained by blending the organic silicon compounds of Examples 1 and 2.

| Formulation 1: Oily foundation | |
|---|---|
| | % by weight |
| Part (A) | |
| Kaolin | 20.0 |
| Titanium oxide | 12.0 |
| Sericite | 8.0 |
| Coloring pigment | suitable |
| Part (B) | |
| Carnauba wax | 4.0 |

| Formulation 1: Oily foundation | |
|---|---|
| | % by weight |
| Dimethylpolysiloxane (viscosity 50 cSt at 25° C.) | 5.0 |
| 48% octamethylcyclotetrasiloxane solution of the organic silicon compound in Example 1 | 8.0 |
| Octamethylcyclotetrasiloxane | 42.0 |
| Sorbitan sesquioleate | 1.0 |
| Part (C) | |
| Flavor | suitable |

The ingredients of Part (B) were agitated at 70° C. into a uniform solution, to which the ingredients of Part (A) were added and dispersed therein by agitation. After cooling, the mixture was milled three rounds in a three roll mill. Part (C) was finally added, obtaining an oily foundation.

The oily foundation was improved in UV absorption and well spreadable, offering a placid pleasant feel to the skin.

| Formulation 2: Solid foundation | |
|---|---|
| | % by weight |
| Part (A) | |
| Titanium oxide | 20.0 |
| Mica | 36.0 |
| Sericite | 10.0 |
| Talc | 10.0 |
| Coloring pigment | suitable |
| Part (B) | |
| Dimethylpolysiloxane (viscosity 50 cSt at 25° C.) | 12.5 |
| 45% octamethylcyclotetrasiloxane solution of the organic silicon compound in Example 2 | 10.0 |
| Lipophilic glycerin monooleate | 1.5 |
| Methyl p-hydroxybenzoate | suitable |
| Flavor | suitable |

The ingredients of Part (A) were milled in a twin roll mill and then combined with Part (B) in uniform solution form and blended by agitation. The mixture was milled three rounds in a three roll mill, obtaining a solid foundation.

The solid foundation was improved in UV absorption and offered a placid pleasant feel to the skin.

| Formulation 3: Sun screen cream | |
|---|---|
| | % by weight |
| Part (A) | |
| Octamethylcyclotetrasiloxane | 40.0 |
| 48% octamethylcyclotetrasiloxane solution of the organic silicon compound in Example 1 | 20.0 |
| Trimethylsiloxypolysilicate | 25.0 |
| Liquid paraffin | 10.0 |
| Carnauba wax | 5.0 |
| Part (B) | |
| Flavor | suitable |

The ingredients of Part (A) were agitated at 80° C. into a uniform mixture, which was allowed to cool. Addition of Part (A) yielded a sun screen cream. It was improved in UV absorption and offered a placid pleasant feel to the skin.

| Formulation 4: Sun screen emulsion | |
|---|---|
| | % by weight |
| Part (A) | |
| Decamethylcyclopentasiloxane | 7.0 |
| 45% octamethylcyclotetrasiloxane solution of the organic silicon compound in Example 2 | 3.0 |
| Dimethylpolysiloxane (viscosity 350 cSt at 25° C.) | 2.0 |
| Stearic acid | 2.0 |
| Self-emulsifying glycerin monostearate | 1.0 |
| Cetanol | 1.0 |
| Part (B) | |
| Pure water | 72.5 |
| Triethanolamine | 1.0 |
| Propylene glycol | 3.0 |
| Titanium oxide | 5.0 |
| Bentonite | 0.5 |
| Methyl p-hydroxybenzoate | suitable |
| Part (C) | |
| Flavor | suitable |

The ingredients of Part (A) were dissolved by agitation at 80° C. The ingredients of Part (B) were dispersed by agitation at 80° C. With stirring, the dispersion of Part (B) was gradually admitted into the solution of Part (A). The mixture was allowed to cool. Part (C) was finally added, obtaining a sun screen emulsion.

The sun screen emulsion had a placid pleasant feel to the skin.

| Formulation 5: Hair cream | |
|---|---|
| | % by weight |
| Part (A) | |
| Methylphenylpolysiloxane (viscosity 20 cSt at 25° C.) | 17.0 |
| 48% octamethylcyclotetrasiloxane solution of the organic silicon compound in Example 1 | 3.0 |
| Tsubaki oil | 10.0 |
| Haze bee wax | 5.0 |
| Self-emulsifying glycerin monostearate | 3.0 |
| Polyoxyethylene sorbitan monostearate (20 EO) | 3.0 |
| Reduced lanolin | 1.5 |
| Microcrystalline wax | 2.0 |
| Methyl p-hydroxybenzoate | suitable |
| Part (B) | |
| Pure water | 51.0 |
| Borax | 0.5 |
| Glycerin | 3.0 |
| Carboxyvinyl polymer | 0.2 |
| Part (C) | |
| Flavor | 0.8 |

The ingredients of Part (A) were dissolved by agitation at 80° C. The ingredients of Part (B) were dissolved by agitation at 80° C. The solutions of Parts (A) and (B) were mixed and the mixture was cooled to 60° C. Part (C) was finally added to the solution, which was cooled to 30° C., obtaining a hair cream. The cream was improved in UV absorption and had a placid pleasant feel.

| Formulation 6: Lipstick | |
|---|---|
| | % by weight |
| Part (A) | |
| Methylphenylpolysiloxane (viscosity 20 cSt at 25° C.) | 46.5 |
| 45% octamethylcyclotetrasiloxane solution of the organic silicon compound in Example 2 | 10.0 |
| Reduced lanolin | 20.0 |
| Carnauba wax | 4.5 |
| Candelilla wax | 9.0 |
| Seresine wax | 2.5 |
| Haze bee wax | 1.5 |
| Cacao butter | 4.0 |
| Sucrose fatty acid ester | 2.0 |
| Antioxidant | suitable |
| Part (B) | |
| Allantoin | suitable |
| Red No. 3 aluminum lake | suitable |
| Part (C) | |
| Flavor | suitable |

The ingredients of Part (A) were dissolved by agitation at 85° C. A portion of the solution was combined with the ingredients of Part (B). The mixture was milled three rounds in a three roll mill, obtaining a color paste.

The color paste was added to the remainder of Part (A). The mixture was uniformly dispersed by means of a dispersing mixer and then combined with Part (C). The mixture was admitted into a mold and rapidly cooled, obtaining a lipstick. This lipstick had improved UV absorbing capacity, glossy appearance, and placid feel to the lip.

| Formulation 7: Eye shadow | |
|---|---|
| | % by weight |
| Part (A) | |
| Pearl agent | 10.0 |
| Blue ultramarine | 5.0 |
| Part (B) | |
| Dimethylpolysiloxane (viscosity 20 cSt at 25° C.) | 28.0 |
| Octamethylcyclotetrasiloxane | 42.0 |
| 48% octamethylcyclotetrasiloxane solution of the organic silicon compound in Example 1 | 5.0 |
| Reduced lanolin | 5.0 |
| Microcrystalline wax | 5.0 |
| Part (C) | |
| Flavor | suitable |

The ingredients of Part (B) were dissolved by agitation at 80° C. With stirring, the ingredients of part (A) were added to the solution and dispersed therein. Part (C) was added to the mixture. The mixture was milled three rounds in a three roll mill, obtaining a creamy eye shadow. It had improved UV absorbing capacity and placid feel to the skin.

| Formulation 8: Mascara | |
|---|---|
| | % by weight |
| Part (A) | |
| Isoparafin | 20.0 |
| Octamethylcyclotetrasiloxane | 20.0 |
| 45% octamethylcyclotetrasiloxane solution of the organic silicon compound in Example 2 | 7.0 |
| Aluminum stearate | 1.0 |
| Part (B) | |
| Bentonite | 15.0 |
| Methylphenylpolysiloxane (viscosity 20 cSt at 25° C.) | 7.0 |

-continued

| Formulation 8: Mascara | |
|---|---|
| | % by weight |
| Candelilla wax | 10.0 |
| Hydrogenated polybuttene | 5.0 |
| Methyl p-hydroxybenzoate | suitable |
| Part (C) | |
| Kaolin | 5.0 |
| Black iron oxide | 5.0 |

The ingredients of part (A) were agitated into a gel at 80° C. The ingredients of Part (B) were uniformly dispersed by agitation at 80° C. The dispersion was added to the gel of Part (A) and uniformly dispersed therein. After cooling, the ingredients of Part (C) were added. The mixture was milled three rounds in a three roll mill, obtaining a mascara. It had improved UV absorbing capacity and placid feel to the skin.

As is evident from these formulations, the organic silicon compounds of the present invention are effective additives to cosmetic compositions.

Although some preferred embodiments have been described, many modifications and variations may be made thereto in the light of the above teachings. It is therefore to be understood that within the scope of the appended claims, the invention may be practiced otherwise than as specifically described.

We claim:

1. An organic silicon compound having a benzotriazole or benzophenone skeleton, comprising $R^1{}_3SiO_{\frac{1}{2}}$ and $SiO_2$ units as essential units and $R^2SiO_{3/2}$ and $R^3{}_2SiO$ units as optional units, the amounts of $R^2SiO_{3/2}$ and $R^3{}_2SiO$ units each ranging from 0 to 20 mol % of the entire compound, the siloxane units being present in a molar ratio: $(R^1{}_3SiO_{\frac{1}{2}}+R^2SiO_{3/2}+R^3{}_2SiO)/SiO_2$ of from 0.5 to 1.5, 1 to 33 mol % of the total quantity of the organic groups represented by $R^1$, $R^2$ and $R^3$ being selected from the groups of the following structural formulae (1) through (7), the remainder being a monovalent saturated or unsaturated organic group having 1 to 18 carbon atoms, (1)

(2)

(3)

(4)

(5)

(6)

(7)

wherein
$R^4$ is a hydrogen atom or a monovalent saturated hydrocarbon group having 1 to 5 carbon atoms,
$R^5$ is selected from the group consisting of monovalent saturated or unsaturated organic groups having 1 to 18 carbon atoms, halogen atoms, alkoxy, carboxy, hydroxy, and amino groups,
$R^6$ is a hydrogen atom or a monovalent saturated or unsaturated hydrocarbon group having 1 to 10 carbon atoms,
letter a is an integer of from 0 to 3, b is an integer of from 0 to 4, and c is an integer of from 0 to 5.

2. A cosmetic composition containing an organic silicon compound as set forth in claim 1.

3. The compound according to claim 1, wherein said monovalent saturated or unsaturated organic group represented by $R^1$, $R^2$, and $R^3$ is selected from the group consisting of aliphatic hydrocarbon groups, saturated cycloaliphatic hydrocarbon groups and aromatic hydrocarbon groups.

4. The compound according to claim 1, wherein said monovalent organic group represented by $R^1$, $R^2$, and $R^3$ is selected from the group consisting of methyl, ethyl, propyl, butyl, pentyl, hexyl, heptyl, octyl, nonyl, decyl, dodecyl, tetradecyl, hexadecyl, octadecyl, cyclopentyl, cyclohexyl, phenyl, and tolyl.

5. The compound according to claim 1, wherein at least 50 mol % of the total moles of $R^1$, $R^2$, and $R^3$ are a methyl group.

6. The compound according to claim 1, wherein said monovalent saturated or unsaturated organic group represented by $R^1$, $R^2$, and $R^3$ is a methyl group.

7. The compound according to claim 1, wherein said monovalent saturated or unsaturated organic group represented by $R^5$ is selected from the group consisting of aliphatic hydrocarbon groups, saturated cycloaliphatic hydrocarbon groups and aromatic hydrocarbon groups.

8. The compound according to claim 1, wherein said monovalent organic group represented by $R^5$ is selected from the group consisting of methyl, ethyl, propyl, butyl, pentyl, hexyl, heptyl, octyl, nonyl, decyl, dodecyl, tetradecyl, hexadecyl, octadecyl, cyclopentyl, cyclohexyl, phenyl, and tolyl.

9. The compound according to claim 1, wherein said alkoxy group represented by $R^5$ is selected from the group consisting of methoxy and ethoxy.

10. The compound according to claim 1, wherein said monovalent saturated or unsaturated group represented by $R^6$ is selected from the group consisting of aliphatic hydrocarbon groups, saturated cycloaliphatic hydrocarbon groups and aromatic hydrocarbon groups.

11. The compound according to claim 1, wherein said monovalent saturated or unsaturated organic group represented by $R^6$ is selected from the group consisting of methyl, ethyl, propyl, butyl, pentyl, hexyl, heptyl, octyl, nonyl, decyl, cyclopentyl, cyclohexyl, phenyl, and tolyl.

12. The compound according to claim 1, wherein said total quantity of organic groups representing a group of said formulae (1) through (7) is in range of 1 to 20 mol %.

13. The method according to claim 1, wherein said molar ratio: $(R^1{}_3SiO_{\frac{1}{2}}+R^2SiO_{3/2}+R^3{}_2SiO)/SiO_2$ ranges from 0.6/1 to 1.3/1.

14. A cosmetic composition containing an organic silicon compound as claimed in claim 4.

15. A cosmetic composition containing an organic silicon compound as claimed in claim 5.

16. A cosmetic composition containing an organic silicon compound as claimed in claim 6.

17. A cosmetic composition containing an organic silicon compound as claimed in claim 8.

18. A cosmetic composition containing an organic silicon compound as claimed in claim 11.

19. A cosmetic composition containing an organic silicon compound as claimed in claim 12.

20. A cosmetic composition containing an organic silicon compound as claimed in claim 13.

* * * * *